US012394524B2

United States Patent
Ng et al.

(10) Patent No.: US 12,394,524 B2
(45) Date of Patent: *Aug. 19, 2025

(54) SYSTEMS AND METHODS FOR ANALYSIS OF MEDICAL IMAGES FOR SCORING OF INFLAMMATORY BOWEL DISEASE

(71) Applicant: Iterative Scopes, Inc., Cambridge, MA (US)

(72) Inventors: Jonathan Ng, Cambridge, MA (US); Jean-Pierre Schott, Cambridge, MA (US); Perikumar Mukundbhai Javia, Cambridge, MA (US); Austin Wang, Cambridge, MA (US); Neelima Chavali, Cambridge, MA (US); Thomas Varner, Cambridge, MA (US); Lavi Erisson, Cambridge, MA (US); Sloane Allebes Phillips, Cambridge, MA (US); Daniel Wang, Cambridge, MA (US)

(73) Assignee: Iterative Scopes, Inc., Cambridge, MA (US)

( * ) Notice: Subject to any disclaimer, the term of this patent is extended or adjusted under 35 U.S.C. 154(b) by 1016 days.

This patent is subject to a terminal disclaimer.

(21) Appl. No.: 17/164,418

(22) Filed: Feb. 1, 2021

(65) Prior Publication Data
US 2022/0028547 A1 Jan. 27, 2022

Related U.S. Application Data

(60) Provisional application No. 63/055,125, filed on Jul. 22, 2020.

(51) Int. Cl.
*G16H 50/20* (2018.01)
*A61B 1/31* (2006.01)
(Continued)

(52) U.S. Cl.
CPC ............... *G16H 50/20* (2018.01); *A61B 1/31* (2013.01); *A61B 5/7267* (2013.01);
(Continued)

(58) Field of Classification Search
CPC ........ G16H 50/20; G16H 10/60; G16H 50/30; G06F 18/24; G06F 18/21; G06N 3/08
(Continued)

(56) References Cited

U.S. PATENT DOCUMENTS 7,236,623 B2 * 6/2007 Chapoulaud ...... G06F 18/24317
382/133
8,768,024 B1 * 7/2014 Zingman .......... A61B 1/000094
348/45

(Continued)

OTHER PUBLICATIONS

Vashist et al. ("Endoscopic scoring indices for evaluation of disease activity in ulcerative colitis", John Wiley & Sons, 2018, pp. 1-42) (Year: 2018).*

(Continued)

*Primary Examiner* — Iftekhar A Khan
(74) *Attorney, Agent, or Firm* — Fish & Richardson P.C.

(57) ABSTRACT

This specification describes systems and methods for performing endoscopy, obtaining medical images for inflammatory bowel disease (IBD) and scoring severity of IBD in patients. The methods and systems are configured for using machine learning to determine measurements of various characteristics related to IBD. The methods and systems may also obtain and incorporate electronic health data of patients along with endoscopic data to use for scoring purposes.

20 Claims, 6 Drawing Sheets

(51) Int. Cl.

| | |
|---|---|
| *A61B 5/00* | (2006.01) |
| *G06F 18/21* | (2023.01) |
| *G06F 18/24* | (2023.01) |
| *G06N 3/08* | (2023.01) |
| *G06T 7/00* | (2017.01) |
| *G16B 20/00* | (2019.01) |
| *G16B 30/00* | (2019.01) |
| *G16B 40/20* | (2019.01) |
| *G16H 10/20* | (2018.01) |
| *G16H 10/40* | (2018.01) |
| *G16H 10/60* | (2018.01) |
| *G16H 30/20* | (2018.01) |
| *G16H 30/40* | (2018.01) |
| *G16H 50/30* | (2018.01) |
| *G16H 50/50* | (2018.01) |
| *G16H 50/70* | (2018.01) |
| *G16H 70/60* | (2018.01) |

(52) U.S. Cl.
CPC ............ *A61B 5/7275* (2013.01); *G06F 18/21* (2023.01); *G06F 18/24* (2023.01); *G06N 3/08* (2013.01); *G06T 7/0012* (2013.01); *G16B 20/00* (2019.02); *G16B 30/00* (2019.02); *G16B 40/20* (2019.02); *G16H 10/60* (2018.01); *G16H 30/20* (2018.01); *G16H 30/40* (2018.01); *G16H 50/30* (2018.01); *G16H 50/50* (2018.01); *G16H 50/70* (2018.01); *G16H 70/60* (2018.01); *G06T 2207/10068* (2013.01); *G06T 2207/20081* (2013.01); *G06T 2207/30092* (2013.01); *G06V 2201/03* (2022.01); *G16H 10/20* (2018.01); *G16H 10/40* (2018.01)

(58) Field of Classification Search
USPC .............................................................. 703/6
See application file for complete search history.

(56) References Cited

U.S. PATENT DOCUMENTS

| | | | |
|---|---|---|---|
| 9,324,145 B1* | 4/2016 | Cherevatsky | A61B 1/000094 |
| 9,613,402 B2* | 4/2017 | Takahashi | G06T 5/70 |
| 10,606,982 B2* | 3/2020 | Guo | G06V 20/70 |
| 11,353,456 B2* | 6/2022 | Oved | A61B 17/00234 |
| 11,574,401 B2* | 2/2023 | Aoyama | G16H 50/20 |
| 11,991,478 B2* | 5/2024 | Kamon | A61B 1/000094 |
| 2003/0208107 A1* | 11/2003 | Refael | A61B 1/041 |
| | | | 600/300 |
| 2007/0255095 A1* | 11/2007 | Gilreath | A61B 5/4255 |
| | | | 600/102 |
| 2008/0085524 A1* | 4/2008 | Lois | G01N 33/74 |
| | | | 435/7.1 |
| 2008/0089881 A1* | 4/2008 | Li | A61P 29/00 |
| | | | 506/14 |
| 2008/0147087 A1* | 6/2008 | Horn | A61B 5/073 |
| | | | 606/130 |
| 2008/0242931 A1* | 10/2008 | Nishino | A61B 1/00016 |
| | | | 600/117 |
| 2009/0196476 A1* | 8/2009 | Inoue | A61B 1/04 |
| | | | 382/128 |
| 2010/0046816 A1* | 2/2010 | Igual-Munoz | G06V 10/7635 |
| | | | 382/128 |
| 2011/0045476 A1* | 2/2011 | Barken | G01N 33/6893 |
| | | | 435/7.1 |
| 2011/0164126 A1* | 7/2011 | Ambor | H04N 7/185 |
| | | | 348/E7.085 |
| 2011/0212104 A1* | 9/2011 | Beaumont | C07K 16/2866 |
| | | | 530/387.3 |
| 2012/0095331 A1* | 4/2012 | Ohashi | G06T 7/0014 |
| | | | 600/425 |
| 2013/0070986 A1* | 3/2013 | Peleg | G06F 18/41 |
| | | | 382/128 |
| 2016/0125135 A1* | 5/2016 | Ramanathan | G06F 16/5846 |
| | | | 705/3 |
| 2016/0224750 A1* | 8/2016 | Kethman | G16H 40/63 |
| 2017/0233809 A1* | 8/2017 | Hackney | G01N 33/573 |
| | | | 424/133.1 |
| 2017/0358078 A1* | 12/2017 | Hoff | G06T 7/0012 |
| 2019/0304093 A1* | 10/2019 | Duval | G16H 30/40 |
| 2020/0342958 A1* | 10/2020 | Mcgovern | G16B 20/20 |
| 2021/0153808 A1* | 5/2021 | Tada | G06T 7/0016 |
| 2021/0174958 A1* | 6/2021 | Drake | G16H 20/10 |
| 2021/0207217 A1* | 7/2021 | Chang | C12Q 1/6883 |
| 2021/0213088 A1* | 7/2021 | Blain | A61P 1/00 |
| 2021/0398676 A1* | 12/2021 | Evans | G16H 15/00 |
| 2022/0002805 A1* | 1/2022 | Baribaud | C12Q 1/6883 |
| 2022/0020496 A1* | 1/2022 | Saito | G06T 7/0012 |
| 2022/0028059 A1* | 1/2022 | Ng | A61B 1/0005 |
| 2022/0028550 A1* | 1/2022 | Ng | A61B 1/000094 |
| 2022/0181027 A1* | 6/2022 | Ackerman | G16H 50/20 |
| 2022/0296081 A1* | 9/2022 | Nygaard Espeland | G06F 18/24133 |
| 2022/0351838 A1* | 11/2022 | Pedemonte | G06T 11/00 |
| 2022/0364171 A1* | 11/2022 | Vermeire | C07K 16/2839 |
| 2023/0033021 A1* | 2/2023 | Jones | A61K 31/445 |
| 2023/0036392 A1* | 2/2023 | Kim | A23L 33/40 |
| 2023/0148834 A1* | 5/2023 | Baras | G06V 10/764 |
| | | | 382/128 |
| 2023/0154580 A1* | 5/2023 | Wang | G16H 50/20 |
| | | | 382/118 |

OTHER PUBLICATIONS

Stidham et al., jamanetwork.com [online], "Performance of a Deep Learning Model vs Human Reviewers in Grading Endoscopic Disease Severity of Patients With Ulcerative Colitis," May 17, 2019, retrieved on Sep. 2, 2021, retrieved from URL<https://jamanetwork.com/journals/jamanetworkopen/fullarticle/2733432>, 10 pages.

Takenaka et al., "Development and Validation of a Deep Neural Network for Accurate Evaluation of Endoscopic Images From Patients with Ulcerative Colitis," Gastroenterology, Jun. 2020, 158(8):2150-2157.

\* cited by examiner

SYSTEMS AND METHODS FOR ANALYSIS OF MEDICAL IMAGES FOR SCORING OF INFLAMMATORY BOWEL DISEASE

CLAIM OF PRIORITY

This application claims priority under 35 U.S.C. § 119(e) to U.S. Patent Application Ser. No. 63/055,125, filed on Jul. 22, 2020, the entire contents of which are hereby incorporated by reference.

TECHNICAL FIELD

This disclosure generally relates to systems and methods for scoring and quantifying disease, potential malignancies, such as inflammation, and predicting disease progression and treatment outcomes.

BACKGROUND

Inflammatory Bowel Disease (IBD) is a disease which results from a dysregulated and excessive autoimmunity to the intestinal microbiome. IBD is chronic, idiopathic and has a high burden of disease. Patients are susceptible to various anatomical complications during the natural course of disease, as well as opportunistic infections of the gut, which may result in relapses. There are two distinct categories of IBD with differentiable clinical presentation; ulcerative colitis (UC) and Crohn's Disease (CD). Currently, IBD affects 1.4 million Americans and occurs at a prevalence rate of 396 per 100,000 individuals worldwide. IBD tends to appear in patients aged in their 20s to 40s with a demographic peak at 20-30 years for CD and 30-40 years for UC. Up to 15% of patients present with IBD at old age (>65 years).

Endoscopy refers to a nonsurgical procedure used to examine a person's digestive tract. Typically, an endoscope, which is a flexible tube that includes a light and camera, is placed within a patient's digestive tract so that a doctor can view images (e.g., still images and/or video) of the patient's digestive tract. For example, during an upper endoscopy, an endoscope is passed through the mouth and throat into the esophagus of a patient, allowing a doctor to view the esophagus, stomach, and upper part of the small intestine. Similarly, an endoscope can be passed into the large intestine of a patient through the rectum to examine this area of the intestine (e.g., a colonoscopy). Endoscopic procedures allow physicians to evaluate several medical conditions, such as causes of stomach pain, appearances of ulcers, bleeding in the digestive tract, and detection of potential malignancies (e.g., polyps). Endoscopic procedures are a key endpoint for healthcare providers to measure IBD outcome and activity. The FDA also increasingly views endoscopic endpoints (as opposed to patient reported symptoms) as a key measure of drug efficacy and performance for IBD related clinical trials.

Several classification methods have developed to better measure and segment IBD patient populations into groups based on severity and disease progression. Among these classification methods are the Mayo Score (UC classification), UCEIS (UC classification), CDAI (CD classification), CDEIS (CD classification). Many other classification systems also exist and generally incorporate clinical and endoscopic components. Currently classification scoring is done by the physician or outsourced to centralized reading platforms. However, such scoring can be highly subjective between different people and intrarater variability is fairly high. New approaches to classifying endoscopic related IBD data have been suggested in research involving computer vision and machine learning techniques as a way to provide more objective and precise classification scores.

Computer vision (CV) is one of the research fields that has been impacted the most by the AI revolution that has taken place over the past few years. Part of the reason is the effectiveness (and efficiency) of convolutional neural networks (CNNs) at distilling information from images. Convolutions can be computed very quickly by graphic processing units (GPUs); have few parameters; and can capture complex patterns at multiple scales, when integrated with deep neural networks.

Previous approaches include attempting to predict Mayo scores from single still frames, where the ground truth was obtained through the majority vote of 3 human experts. A deep learning image classification model was pre-trained on millions of natural. The results degraded in a 4-class setup (approx. 75% accuracy). In another example, approximately 40,000 biopsies and endoscopic images from corresponding anatomical locations were analyzed. Image classification is used to find UCEIS scores. For UCEIS, they have sub-scores for the different descriptors. A 90% accuracy for endoscopic remission, 93% for histologic remission, and ICC=0.92 for UCEIS.

These approaches attempt to make predictions from images (e.g., remission, no remission, Mayo=1, etc.). This has long been one of the main problems studied by the CV literature.

SUMMARY

This specification describes systems and methods for scoring medical images for inflammatory bowel disease (IBD). A data processing system is configured to obtain endoscopy data from an endoscopy procedure. The endoscopy data includes medical image data, including video data. The data processing system is configured to perform one or more image processing operations to extract relevant data from the video data and label the video data. The data processing system includes a machine learning module. The machine learning module is configured to receive the labeled video data and perform an analysis of the video data according to one or more approaches. The machine learning module is configured to determine values of various characteristics and features related to IBD that can be used for predicting disease progression and activity. The data processing system is configured to obtain and incorporate electronic health data of patients in combination with the endoscopic video data for scoring purposes.

The systems and methods described in this specification provide one or more of the following advantages.

Compared to current standard of manual review, the data processing system is able to provide accurate scoring while taking many different data modalities into account. For example, the data processing system is configured to combine image classification with analysis of other data, including omics data, registries data, and electronic medical records (EMR) data. The data processing system is more accurate than previous models and includes model interpretability. For example, the data processing system is configured to combine analysis of different kinds of symptoms and colon conditions that are exhibited and note locations within an image frame. For example, the data processing system can identify instances of obliterated vascular patterns in the middle of the frame and one or more instances of bleeding on an edge of the frame. The data processing system is configured to generate scoring data that reflect detection of both symptoms, rather than only one of the two symptoms. The data processing system is configured to overcome limitations of relying only on image classification to generate predictions or scores indicative of IBD. For example, the data processing system overcomes these limitations because objects may not occupy most of the field of view for endoscopy images. In such cases, location specific labels (like segmentations or bounding boxes) are much more informative than image-level labels, even if the amount of location-specific data provided is less than for corresponding label data. Additionally, the data processing system is configured to generate scoring based on data included in Electronic Medical Records (EMR) or Electronic Health Records (EHR), molecular data, omics data, patient reported data and other patient data (e.g., wearables data, data from patient devices, and such similar data where relevant).

Additionally, the data processing system reduces variability in analysis (e.g., relative to manual analysis) by providing computer generated automated scoring. Currently, a large variability exists between how humans interpret video data. Central readers can be qualified for analyzing patient data when achieving intrarater agreement of only 60%. Currently the assumption is that intrarater variability is somewhere between 10-35%. Relatively high variability results in issues with patient outcomes. For example, because trials are powered to primary end points, the greater the variability, the greater the number of patients that need to be recruited into the trial. This adds tremendous amounts of cost to pharmaceutical companies, not to mention, the bottleneck of not having biologic naïve patients on whom to test these new drugs. Furthermore, scoring is important to track and monitor disease progression in patients. More accurate and precise scoring can enable more precise patient monitoring and quicker and more effective treatment adjustments, which generally leads to better patient outcomes. Consistent scoring can also reduce the time and cost to develop new biologic treatments for IBD because reducing scoring variability will reduce the number of patients needed for pharma trials.

To overcome this issues, the data processing system is configured to provide a more objective, consistent score for endoscopic images, relative to existing scores of such data, by incorporating machine learning and computer vision techniques that reduce intrarater and interrater variability. The data processing system can provide a composite score which captures IBD disease progression (e.g., disease activity) more accurately than existing scoring systems (e.g., Mayo scores, USCIS, etc.). For example, the data processing system is configured to annotate features of colonoscopy video data and use these features for score generation. The data processing system is configured to generate scores that are consistent over different iterations and for different patients based on the analysis of many different types of data.

The data processing system is configured to use regression rather than classification models. This is because a classification model generally penalizes all mistakes equally. The loss functions within the regression algorithm are driven by clinical practices, instead of pure statistical analysis, and penalizes more heavily some label transition than other. For example in the Mayo scoring system, a 4 level scoring scale, where 0 means normal, and 2 means moderate disease, the threshold for treatment, a misclassification within the groups of (0, 1) and (2, 3) is less severe than across group such 1 to 2 or vice versa as scores of 0 and 1 are indicative of inactive disease and scores of 2 and 3 are indicative of active disease. The data processing system regression approach is configured to ensure that any penalty applied is proportional to the size and type of the error.

In a general aspect, the systems and methods are configured for regression of score values (e.g., Mayo scores) and other clinical variables of interest (including histologic remission) from video data including videos representing entire colonoscopies. The data processing system meta-architectures can be configured to receive a temporal input of feature vectors derived from frames by a convolutional neural network (CNN) or a long short-term memory (LSTM) model, and classify the whole video. The meta-architecture of the data processing system enables the data processing system to configure to regress score data (e.g., Mayo scores), but also any other clinical variable of interest.

In an example embodiment, the data processing system is configured for improvement of frame-level regression with recurrent neural networks (RNN). The frame-level performance is improved by including temporal information in machine learning models. This can be achieved by extending the single-frame architecture into a bi-directional model.

The temporal models described in this specification can improve classification at frame, clip, a subset of consecutive frames that characterize an event, and video levels. At the frame level, classifying frames independently is generally suboptimal, as one ignores all the context in preceding and subsequent frames. The recurrent neural networks that are applied by the data processing system combine one frame with a "state" that summarizes the past. In this way, the data processing system accounts temporal information. Bi-directional recurrent networks such as LSTM and GRU of the data processing system are configured to greatly outperform analysis of frames one of the time. The data processing system is configured to, at the clip level, apply an ad hoc rules approach. For example, the data processing system can determine that a score value (e.g., a Mayo score) for a video should be 3 if more than 10% of video still frames are scored as having a score value of 3 can be suboptimal in comparison to machine learning approaches that learn to predict scores at the clip level and subsequently at the video level, building on top of frame-level scores. Once the data processing system trains a CNN at the frame level, this meta-approach annotates at the video clip level and can avoid the requirement of annotating individual frames, saving processing bandwidth and reducing processing timeframes.

Adequate representation of all score types results in a translation of video images into a score. The data processing system is configured to collect annotations at in detail, such as bounding boxes, segmentations of informative features such as bleeding, ulcers, etc., and so forth. The detailed analysis enables improvement over time of the meta-architectures. Annotation can balance different types of annotations (e.g., at the frame level including bounding boxes, segmentations, etc.) machine learning training set that adequately trains the data processing system to predict disease progression. In given training data set, a majority (e.g., at least 60%) of cases generally have positive score value indicating the presence of IBD symptoms. Generally, only a relatively small percentage (e.g., less than 20% of the training data set or less) includes video data associated symptoms and thus no score (e.g., a Mayo score of 0). Other proportions are possible (e.g. less than 15%, less than 10%, etc.). Additional data that can be valuable to enrich the machine learning model include: patient demographic data (age, race, gender, etc.), patient medical history, patient reported outcomes (PROs), concomitant medications, labs, biomarker data, and other molecular data.

Each of the following embodiments are configured to enable one or more of the foregoing advantages.

In a general aspect, a process for treatment of inflammatory bowel disease (IBD) in a patient and determining a score of disease activity includes obtaining image data including endoscopic images of a gastrointestinal tract (GI) of a patient. The process includes determining one or more features to extract from the image data, the features each representing a physical parameter of the GI tract. The process includes extracting the one or more features from the image data to form a feature vector. The process includes selecting a machine learning model based on the one or more features included in the feature vector. The process includes processing the feature vector using the machine learning model, the machine learning model being trained with labeled image data representing instances of symptoms of IBD being in the GI tract, the labeled image data associating scores representing a severity of IBD the respective instances of the symptoms. The process includes determining, based on the processing, a score representing a severity of IBD in the patient indicated by the image data. The process includes storing, in a data store, the score in association with the image data.

In some implementations, determining the score comprises determining one or more frame level annotations corresponding to individual frames of a video of the image data; determining one or more case level annotations for the video of the image data; and determining, based on the one or more frame level annotations and the one or more case level annotations, the score associated with the video of the image data.

In some implementations, the one or more features comprise values representing at least one of: a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal. The score represents a severity of IBD in the patient is based on the values of the one or more features.

In some implementations, the process includes receiving electronic medical records (EMR) data for the patient, the EMR data including medical information about the patient, wherein the machine learning model is trained with labeled EMR data associating values of medical information of patients with respective severity of IBD in the patients. The process includes extracting one or more values from the EMR data to form an EMR feature vector. The process includes processing, by the machine learning model or by a second machine learning model in addition to the machine learning model, the EMR feature vector. The process includes generating an updated score representing the severity of IBD in the patient indicated by the EMR data.

In some implementations, the one or more features of the EMR feature vector comprise values representing at least one of: an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

In some implementations, the process includes receiving registry data for the patient, the registry data including patient data across patient populations, wherein the machine learning model is trained with labeled registry data associating values of for patient populations with respective severity of IBD in particular patients of the patient populations. The process includes extracting one or more values from the registry data to form a registry feature vector. The process includes processing, by the machine learning model or by a second machine learning model in addition to the machine learning model, the registry feature vector. The process includes generating an updated score representing the severity of IBD in the patient indicated by the registry data.

In some implementations, the one or more features of the registry feature vector comprise values representing at least one of: results and other data from studies, experiments, and clinical trials that test treatment regimens that are associated with the patient including one or more of drug therapy, physical therapy, or surgery, specific diagnoses associated with the patient, procedures, and application of drugs associated with the patient.

In some implementations, the process includes receiving omics data for the patient, the omics data including genetic or molecular profiles of patient populations. The machine learning model is trained with labeled omics data associating values of genetic or molecular profiles with respective severity of IBD in the patients of the patient populations. The process includes extracting one or more values from the omics data to form an omics feature vector. The process includes processing, by the machine learning model or by a second machine learning model in addition to the machine learning model, the omics feature vector. The process includes generating an updated score representing the severity of IBD in the patient indicated by the omics data.

In some implementations, the one or more features of the omics feature vector comprise values representing at least one of: transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfite sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

In some implementations, the machine learning model comprises a convolutional neural network (CNN), and wherein the each of the instances of symptoms of IBD contributes to an activation value for inputting into a layer of the CNN.

In some implementations, processing the feature vector comprises performing a classification with detection bounding boxes and segmentation pixel-wise masks on the image data.

In some implementations, the process includes generating the machine learning model by: receiving image data including ground truth scores, labeling the image data, performing frame sampling and score assignment to the frames, applying training data to the machine learning model at a frame level and at a case level, optimizing the machine learning model with validation data at the frame level and the case level, applying test data that is not annotated, and performing case level evaluation of the test data.

In a general aspect, a system for treatment of inflammatory bowel disease (IBD) in a patient and determining a score of disease activity includes one or more processing devices and a memory storing instructions that, when executed by the one or more processing devices, cause the one or more processing devices to perform the following operations. The operations include obtaining image data including endoscopic images of a gastrointestinal tract (GI) of a patient. The operations include determining one or more features to extract from the image data, the features each representing a physical parameter of the GI tract. The operations include extracting the one or more features from the image data to form a feature vector. The operations include selecting a machine learning model based on the one or more features included in the feature vector. The operations include processing the feature vector using the machine learning model, the machine learning model being trained with labeled image data representing instances of symptoms of IBD being in the GI tract, the labeled image data associating scores representing a severity of IBD the respective instances of the symptoms. The operations include determining, based on the processing, a score representing a severity of IBD in the patient indicated by the image data. The operations include storing, in a data store, the score in association with the image data.

In some implementations, determining the score comprises determining one or more frame level annotations corresponding to individual frames of a video of the image data; determining one or more case level annotations for the video of the image data; and determining, based on the one or more frame level annotations and the one or more case level annotations, the score associated with the video of the image data.

In some implementations, the one or more features comprise values representing at least one of: a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal. The score represents a severity of IBD in the patient is based on the values of the one or more features.

In some implementations, the operations include receiving electronic medical records (EMR) data for the patient, the EMR data including medical information about the patient, wherein the machine learning model is trained with labeled EMR data associating values of medical information of patients with respective severity of IBD in the patients. The operations include extracting one or more values from the EMR data to form an EMR feature vector. The operations include processing, by the machine learning model or by a second machine learning model in addition to the machine learning model, the EMR feature vector. The operations include generating an updated score representing the severity of IBD in the patient indicated by the EMR data.

In some implementations, the one or more features of the EMR feature vector comprise values representing at least one of: an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

In some implementations, the operations include receiving registry data for the patient, the registry data including patient data across patient populations, wherein the machine learning model is trained with labeled registry data associating values of for patient populations with respective severity of IBD in particular patients of the patient populations. The operations include extracting one or more values from the registry data to form a registry feature vector. The operations include processing, by the machine learning model or by a second machine learning model in addition to the machine learning model, the registry feature vector. The operations include generating an updated score representing the severity of IBD in the patient indicated by the registry data.

In some implementations, the one or more features of the registry feature vector comprise values representing at least one of: results and other data from studies, experiments, and clinical trials that test treatment regimens that are associated with the patient including one or more of drug therapy, physical therapy, or surgery, specific diagnoses associated with the patient, procedures, and application of drugs associated with the patient.

In some implementations, the operations include receiving omics data for the patient, the omics data including genetic or molecular profiles of patient populations. The machine learning model is trained with labeled omics data associating values of genetic or molecular profiles with respective severity of IBD in the patients of the patient populations. The operations include extracting one or more values from the omics data to form an omics feature vector. The operations include processing, by the machine learning model or by a second machine learning model in addition to the machine learning model, the omics feature vector. The operations include generating an updated score representing the severity of IBD in the patient indicated by the omics data.

In some implementations, the one or more features of the omics feature vector comprise values representing at least one of: transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfite sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

In some implementations, the machine learning model comprises a convolutional neural network (CNN), and wherein the each of the instances of symptoms of IBD contributes to an activation value for inputting into a layer of the CNN.

In some implementations, processing the feature vector comprises performing a classification with detection bounding boxes and segmentation pixel-wise masks on the image data.

In some implementations, the operations include generating the machine learning model by: receiving image data including ground truth scores, labeling the image data, performing frame sampling and score assignment to the frames, applying training data to the machine learning model at a frame level and at a case level, optimizing the machine learning model with validation data at the frame level and the case level, applying test data that is not annotated, and performing case level evaluation of the test data.

In a general aspect, one or more non-transitory computer readable media store instructions for treatment of inflammatory bowel disease (IBD) in a patient and for determining a score of disease activity. The instructions, when executed by one or more processing devices, cause the one or more processing devices to perform the following operations.

The operations include obtaining image data including endoscopic images of a gastrointestinal tract (GI) of a patient. The operations include determining one or more features to extract from the image data, the features each representing a physical parameter of the GI tract. The operations include extracting the one or more features from the image data to form a feature vector. The operations include selecting a machine learning model based on the one or more features included in the feature vector. The operations include processing the feature vector using the machine learning model, the machine learning model being trained with labeled image data representing instances of symptoms of IBD being in the GI tract, the labeled image data associating scores representing a severity of IBD the respective instances of the symptoms. The operations include determining, based on the processing, a score representing a severity of IBD in the patient indicated by the image data. The operations include storing, in a data store, the score in association with the image data.

In some implementations, determining the score comprises determining one or more frame level annotations corresponding to individual frames of a video of the image data; determining one or more case level annotations for the video of the image data; and determining, based on the one or more frame level annotations and the one or more case level annotations, the score associated with the video of the image data.

In some implementations, the one or more features comprise values representing at least one of: a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal. The score represents a severity of IBD in the patient is based on the values of the one or more features.

In some implementations, the operations include receiving electronic medical records (EMR) data for the patient, the EMR data including medical information about the patient, wherein the machine learning model is trained with labeled EMR data associating values of medical information of patients with respective severity of IBD in the patients. The operations include extracting one or more values from the EMR data to form an EMR feature vector. The operations include processing, by the machine learning model or by a second machine learning model in addition to the machine learning model, the EMR feature vector. The operations include generating an updated score representing the severity of IBD in the patient indicated by the EMR data.

In some implementations, the one or more features of the EMR feature vector comprise values representing at least one of: an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

In some implementations, the operations include receiving registry data for the patient, the registry data including patient data across patient populations, wherein the machine learning model is trained with labeled registry data associating values of for patient populations with respective severity of IBD in particular patients of the patient populations. The operations include extracting one or more values from the registry data to form a registry feature vector. The operations include processing, by the machine learning model or by a second machine learning model in addition to the machine learning model, the registry feature vector. The operations include generating an updated score representing the severity of IBD in the patient indicated by the registry data.

In some implementations, the one or more features of the registry feature vector comprise values representing at least one of: results and other data from studies, experiments, and clinical trials that test treatment regimens that are associated with the patient including one or more of drug therapy, physical therapy, or surgery, specific diagnoses associated with the patient, procedures, and application of drugs associated with the patient.

In some implementations, the operations include receiving omics data for the patient, the omics data including genetic or molecular profiles of patient populations. The machine learning model is trained with labeled omics data associating values of genetic or molecular profiles with respective severity of IBD in the patients of the patient populations. The operations include extracting one or more values from the omics data to form an omics feature vector. The operations include processing, by the machine learning model or by a second machine learning model in addition to the machine learning model, the omics feature vector. The operations include generating an updated score representing the severity of IBD in the patient indicated by the omics data.

In some implementations, the one or more features of the omics feature vector comprise values representing at least one of: transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfite sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

In some implementations, the machine learning model comprises a convolutional neural network (CNN), and wherein the each of the instances of symptoms of IBD contributes to an activation value for inputting into a layer of the CNN.

In some implementations, processing the feature vector comprises performing a classification with detection bounding boxes and segmentation pixel-wise masks on the image data.

In some implementations, the operations include generating the machine learning model by: receiving image data including ground truth scores, labeling the image data, performing frame sampling and score assignment to the frames, applying training data to the machine learning model at a frame level and at a case level, optimizing the machine learning model with validation data at the frame level and the case level, applying test data that is not annotated, and performing case level evaluation of the test data.

These and other aspects, features, and implementations can be expressed as methods, apparatus, systems, components, program products, means or steps for performing a function, and in other ways. These and other aspects, features, and implementations will become apparent from the following descriptions, including the claims.

DETAILED DESCRIPTION

Figure 1:
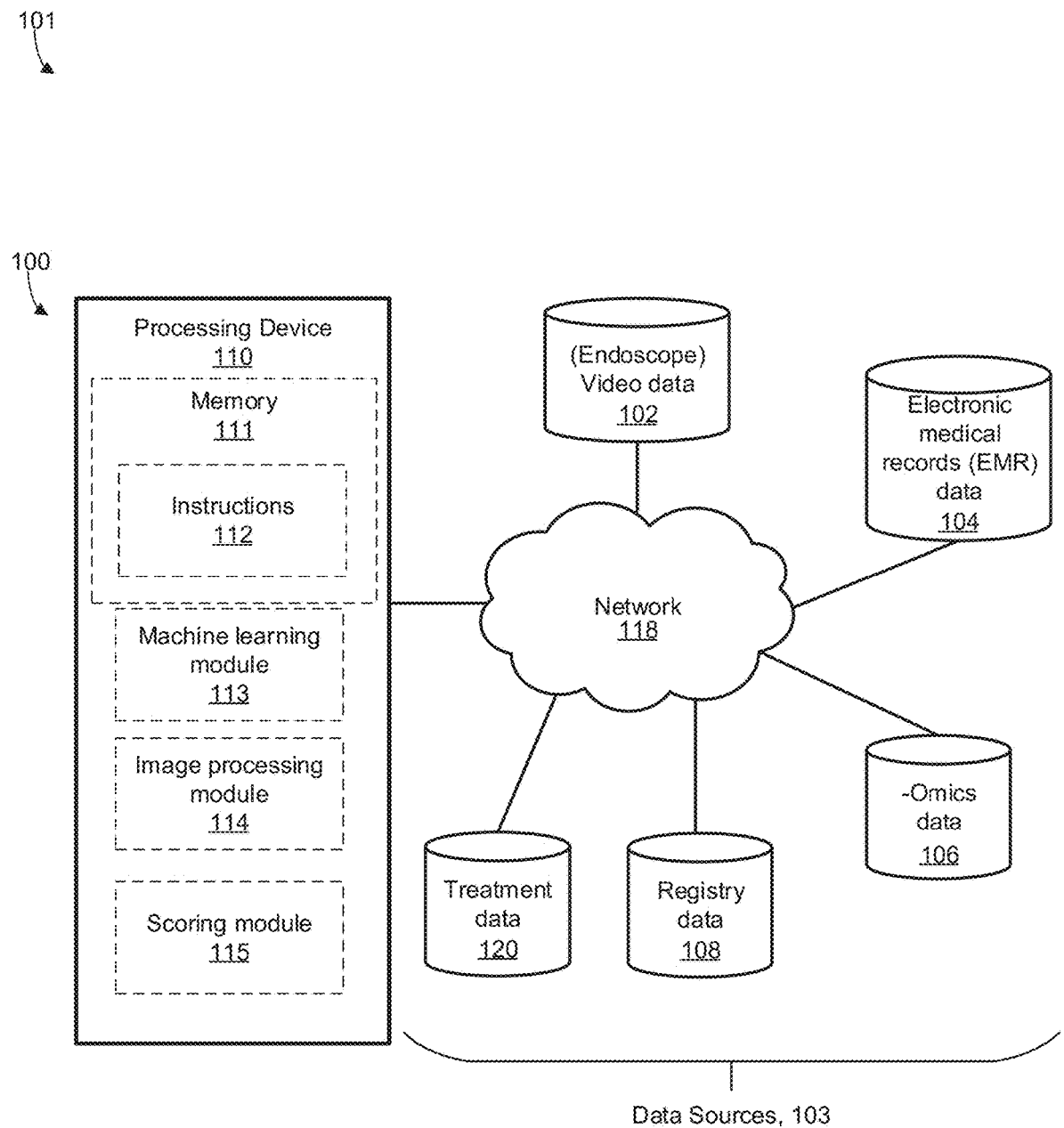
FIG. 1 shows a data processing system for scoring IBD, prediction disease progression, and recommending one or more treatments for IBD.

FIG. 1 shows an example of a data processing system 100 configured to execute one or more processes for an automated analysis of endoscopic and other health data for inflammatory bowel disease (IBD) classification and treatment. The data processing system includes a processing device 110, a memory 111 (or a computer readable hardware storage device) configured to host instructions 112, a machine learning system 113 configured to execute one or more trained machine learning platforms, an image processing module 114, and a scoring module 115.

The data processing system 100 is configured for using machine learning (e.g. of the machine learning module 113, described below) to determine measurements of various characteristics related to IBD. The data processing system 100 is configured to obtain and incorporate data from various sources for training the machine learning system 113, performing scoring (e.g., by scoring module 115) of endoscope video data 102. For example, the data processing system 100 includes electronic health records or electronic medical records (EMR) data 104 of patients in addition to video (endoscope) data 102 to use for scoring. The data processing system 100 also accesses -omics data 106 and registry data 108 for training the machine learning system 113 and performing scoring. In some implementations, functions of one or more of modules 113, 114, and/or 115, can be combined in part or in whole.

The data processing system 100 processes data from one or more of data sources 103. The data sources include video data 102, electronic medical records 104, -omics data 106, registry data 108, and treatment data 120. Each of these data sources 103 is subsequently described in further detail. These data sources 103 can be used individually or in any combination for generating enhanced scores for IBD. For example, video data 102 alone may be sufficient to generate a confident score for a particular patient. In another example, video data 102 can be supplemented with EMR data 104, -omics data 106, etc. to increase confidence in a particular score or in an initial iteration of scoring.

The data processing system 100 is configured to obtain video data 102 from an endoscopic tower or endoscopic processing unit (not shown). The endoscopic tower includes an imaging device that is configured to capture image data or video data 102. In some implementations, the imaging device is an endoscope. An endoscope is an illuminated optical, thin, and tubular instrument (e.g., borescope) used to examine internal organs like the throat or esophagus. The endoscope can be shaped and configured to target specific organs, such as the bladder, kidney, bronchus, colon, and/or pelvis. In some implementations, the endoscope is flexible and includes a camera on one end. The camera can capture image data in the form of still images and/or video. The image or video data 102 can take the form of several data formats, such as RAW, JPEG, PNG, etc. In some implementations, the imaging device includes a digital camera that uses a charge-coupled device (CCD) and/or complementary metal oxide semiconductor (CMOS) to convert photons to electrons for digital processing.

The EMR data 104 includes records associated with individual patients. The EMR data 104 can include self-reported data of the patient. The EMR data 104 can include data obtained from physicians or other medical service providers from interacting with the patient. For example, the EMR data 104 can include a medical history for the patient, such as medical operations the patient has experienced, illnesses the patient has experienced, and physiological data associated with the patient.

The omics data 106 includes genetic or molecular profiles of humans. The omics data 106 includes genomes and the inter-relationships of particular genes. The omics data 106 can be used to provide context to other patient data, such as data acquired from patient registries 108 and/or from EMR data 104.

The registries data 108 includes a clinical data registry, all called a patient registry or disease registry. The registries data 108 includes a database that collects, organizes, and displays healthcare information, generally related to a particular disease and for a patient population. The registries data 108 can be structured such that trends across patient populations are identifiable. For example, the trends can indicate how patients have responded to various IBD treatments. The trends can associate symptoms with scores that have been assigned to those symptoms and how the scores changed in response to particular treatments. The registries data 108 can be combined with the omics data 106 and the EMR data 104 to establish patient trends and track treatment outcomes.

The data processing system 100 is configured to use machine learning techniques to generate a patient score for IBD and to predict disease progression for the patient. The machine learning techniques replicate how physicians interpret endoscope images. For example, the data processing system 100 determines what level of activity of IBD is seen in the images. The level of activity of IBD is based on a number of various sub-classifications represented in images or video obtained from the endoscope. These sub-classifications can include determining the presence of bleeding, inflammation, polyps, or similar symptoms that may occur from IBD. This process is subsequently described in greater detail with respect to the machine learning module 113, the image processing module 114, and the scoring module 115

The data processing system 100 is configured to automate various IBD classification scores (i.e. Mayo Score, etc.), as previously indicated. The data processing system 100 ingests data from various sources, such as image or video data 102, EMR data 104, -omics data 106, and registry data 108. While data sources 102, 104, 106, and 108 are shown in FIG. 1, this list is not exhaustive. Patient data from other sources can also be incorporated into analysis for automation of scoring.

The data processing system 100 is configured to receive video or image data 102 from a procedure (e.g., from a colonoscopy). The image or video data 102 generally includes a sequence of frames, each representing a portion of the colon (or other such patient data). A subset of the frames or images of the video or image data 102 can represent symptoms of IBD. The data processing system 100 is configured to identify the frames or images of the data 102 that represent symptoms and score the video including the frames accordingly.

The image processing module 114 is configured to process the image or video data 102 for identifying the presence of symptoms of IBD. In some implementations, the image processing module 114 is a part of the machine learning module 113, wherein the image processing module extracts data from the images or videos, and the machine learning module 113 performs classification of the extracted data. For example, the image processing module 114 may perform thresholding operations or feature extraction based on signals received from the machine learning module 113 (e.g., setting threshold values or identifying features in the images to extract).

The image processing module 114 can process the images or frames of the video data 102 on an individual basis and/or in combination with one another to identify the presence of IBD symptoms (e.g., bleeding, ulcers or sores, narrowing of the intestines, and so forth). For example, the image processing module 114 can process images frame by frame to identify a symptom presence in the frame (e.g., by signature matching a region of the image to a known signature representing a symptom). In some implementations, the image processing module 114 is configured to identify where in the image the symptom is manifested and identify, to other module (such as the machine learning module 113) which frames or sequence of frames are associated with a symptom.

The image processing module 114 generally is configured to draw bounding boxes or otherwise tag or identify images or frames as representing a symptom. However, how the image processing module 114 identifies the symptoms can be changed or updated based on feedback from the machine learning module 113. For example, the image processing module 114 can extract image data based on thresholds set or adjusted by the machine learning module 113. In some implementations, the machine learning module 113 is configured to update, based on training data, image signature data used for classification of the image or video data.

The image processing module 114 can process groups of frames or images of video data 102 together to identify a symptom. For example, if a symptom appears in single frame of the video, the identification of the symptom may be a false positive. The image processing module 114 can be configured to analyze the image in the context of a previous frame (or series of frames) or a subsequent frame (or series of frames). The image processing module 114 is configured to facilitate extraction and/or recognition, from image data, of features that inform generating of the classification score (e.g., by the machine learning module 113). For example, the image processing module 114 can facilitate detection of bleeding, polyp formation, etc. by applying one or more feature extraction processes using image processing. For example, these processes can include object detection, pixel thresholding, application of filters to the images or portions of the images, and so forth.

The machine learning module 113 is configured to classify the data from the data sources 102, 104, 106, and 108 to determine IBD scores. For example, for video data 102, the machine learning module 113 is configured to regress IBD classification scores from single frames or video clips to enable the scoring module 115 to determine disease severity scores. The machine learning module 113 trains convolutional neural networks (CNNs) to classify video frames or video clips. In some implementations, many frames with scores can be quickly obtained by defining intervals in videos with constant scores. The machine learning module 113 disregards outlying frames (e.g., frames including a representation sprayed water) that may not positively contribute to score regression. The machine learning module 113 is configured for transfer learning to generate a score from features trained with different datasets. For example, an IBD classification score can be updated based on features learned for polyp detection (e.g., based on image processing processes previously described).

In some implementations, the machine learning module 113 includes a plurality of machine learning models. Each model of the plurality can be configured to process data from one of the data sources 103 (e.g., video data 102, EMR 104, omics data 106, and registry data 108) of data available to the data processing system 100. In some implementations, a single machine learning model is configured to receive data from two or more of data sources 103 and use those data in combination for generating a classification output. For example, a machine learning module 113 can receive image data 102 showing that polyps are present in a patient's colon. In addition, the patient may have reported diarrhea symptoms, which can be captured in that patient's EMR data 104. These data together may suggest a stronger IBD classification output. In some implementations, these data are processed by separate models, and the scoring module 115, further described below, combines this data into a common IBD severity score.

In an embodiment, the data processing system 100 performs an automated regression of various IBD classification scores using the machine learning module 113. The machine learning module 113 obtains pre-existing videos and data from data sources 103. The machine learning module 113 annotates these data to derive an updated classification score for the image data 102. The machine learning module 113 receives data 103 from third parties such as hospitals and clinics. The data 103 received can be unstructured data that are transformed for use in the data model (e.g., in one or more machine learning models of the module 113). The data processing system 100 is configured to perform a multi-pronged approach to development of a machine learning model enhancing the generated classification scores based on other features extracted from the data 103. The features extracted from this data can evolve as the models are trained. For example, the machine learning module 113 may be configured for segmenting ulcers at scale, identifying particular trends in the registries data 108, identifying symptoms from patient provided data in EMR records 104, and so forth. The machine learning module 113 passes the classification data to the scoring module 115 to generate a severity score for IBD represented by the endoscopic data and the data from data sources 103.

Based on the analysis by the machine learning module 113, a scoring module 115 of the data processing system 100 is configured to generate a score based on the classification data output from the machine learning module 113. The score of the scoring module 115 represents the presence or absence of symptoms that indicate IBD (or, in some aspects, other diseases that may contribute to IBD or result from IBD). The score can represent a severity of IBD in the patient. For example, low score (e.g., 0) can correspond to a low severity of IBD. A higher score (e.g., 3) can correspond to a high severity of IBD. In an example, the score can represent a probability that the patient has IBD. However, the score value need not be a probability; other values can be used.

The scoring module 115 generates a weighted severity score that is a combination of automated regression and extracted features to represent a validated predictive score. The data processing system 100 is thus configured to generate an increasingly complex endoscopic score based on endoscopic image data 102 in the context of both clinical and molecular data to produce a composite score. The composite score represents the actual clinical state of the patient in context.

The scoring module 115 generally receives feature classification data from the machine learning module 113 and outputs score data. However, the scoring module, and machine learning module 113 can be combined or can be separate modules executed by the processing device 110. In some implementations, the scoring module 115 is a portion of the machine learning module 113. In some implementations, the scoring module receives input from the machine learning module 113 and uses the classifications of one or more machine learning models (e.g., for processing data from different sources 102, 104, 106, and 108) in a voting system to generate the score. In some implementations, the scoring module 115 uses a weighted average of classification values output from machine learning models of the machine learning module 113 or receive from another source. For example, the scoring module 115 may receive a strong classification from a polyp identification machine learning model, and receive data from EMR in which the patient reported bleeding. The scoring data may combine these data to generate a score of higher severity than would be generated from the machine learning model output in isolation. In some implementations, the scoring module 115 can receive conflicting classification outputs form machine learning modules or conflicting data from data sources 103. In this case, the scoring system may generate a low severity score, despite a particular machine learning model outputting a classification output representing a strong indication that a particular symptom is present in the patient. Thus, the inclusion of data from many sources 103 results in a more robust severity score output than a score generated from a particular data source 102, 104, 106, or 108 in isolation.

The data processing system 100 generates the severity during a procedure for the patient (e.g., for each procedure associated with the patient). For example, a severity score is developed from each set of images or videos for the patient. The severity score is generally combined with one or more of registries data 108, EMR data 104, and omics data 106 to develop an overall picture of the patient. As further described below, the EMR data 104, the omics data 106, and the registries data 108 can be used to train the machine learning model along with the video data 102.

The score from the scoring module 115 can be presented to a user of the data processing system 100. The score can be presented as a value (e.g., a number). In some implementations, the score is used to cause a data processing operation to occur based on the value of the score. For example, if the score is above a particular threshold value, the data processing system 100 can be configured to generate an alert, alarm, generate a message, recommend an action, or perform some other operation. For example, if the score exceeds a threshold value, the data processing system 100 can be configured to alert a medical service provider or provide a particular visualization. If the score is below the threshold, the data processing system 100 can be configured to provide a different visualization. In some implementations, a patient record associated with the patient can be automatically updated to include the score.

The computer-readable hardware storage device 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the memory 111 (e.g., computer-readable hardware storage device) includes code-segment (or other executable logic) having executable instructions.

The computer processors 110 can be communicatively coupled to a video capture device and configured to receive spatially arranged image data (e.g., video data) corresponding with one or more images captured by the imaging device. In some implementations, the computer processors 110 include a general purpose processor. In some implementations, the computer processors 110 include at least one applicable inference processor, accelerated processor which can be utilized in half, single, or double precision (16, 32, or 64 bit floating-point) calculation. The computer processor 110 can also include lots of compute unified device architecture (CUDA) cores, etc., or a combination of thereof. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112.

In some implementations, the network 118 enables a cloud-based or web-based system for processing the data. For example, the data processing system 100 can be operated as a web-based service over the network 118. In some implementations, the data sources 103 can be cloud-based and accessible remotely over network 118.

The data processing system can include a display unit (not shown) that is communicatively coupled to the computer processors 110 and configured to show results of the scoring and prediction processes described herein. The display unit can include an electronic display device. In some implementations, the display unit can be configured to act as a touchscreen display device. The display unit is configured to present a user interface. In some implementations, the user interface is a graphical user interface (GUI). The user interface is configured to allow a user of the data processing system 100 to interact with the data processing system 100 through graphical icons and visual indicators. The user interface can use a windows, icons, menus, pointer paradigm (WIMP) to allow a user to interact with the data processing system 100. In some implementations, the user interface 121 cooperates with the 120 to provide a user with a touchscreen GUI. Additionally, or alternatively, the user interface can include one or more input devices such as a mouse and/or keyboard communicatively coupled with the system 100. The user interface can also use a post-WIMP paradigm typically found in touchscreen-based GUIs. In some implementations, the user interface is configured to display images in the form of still photographs and/or videos.

Figure 2:
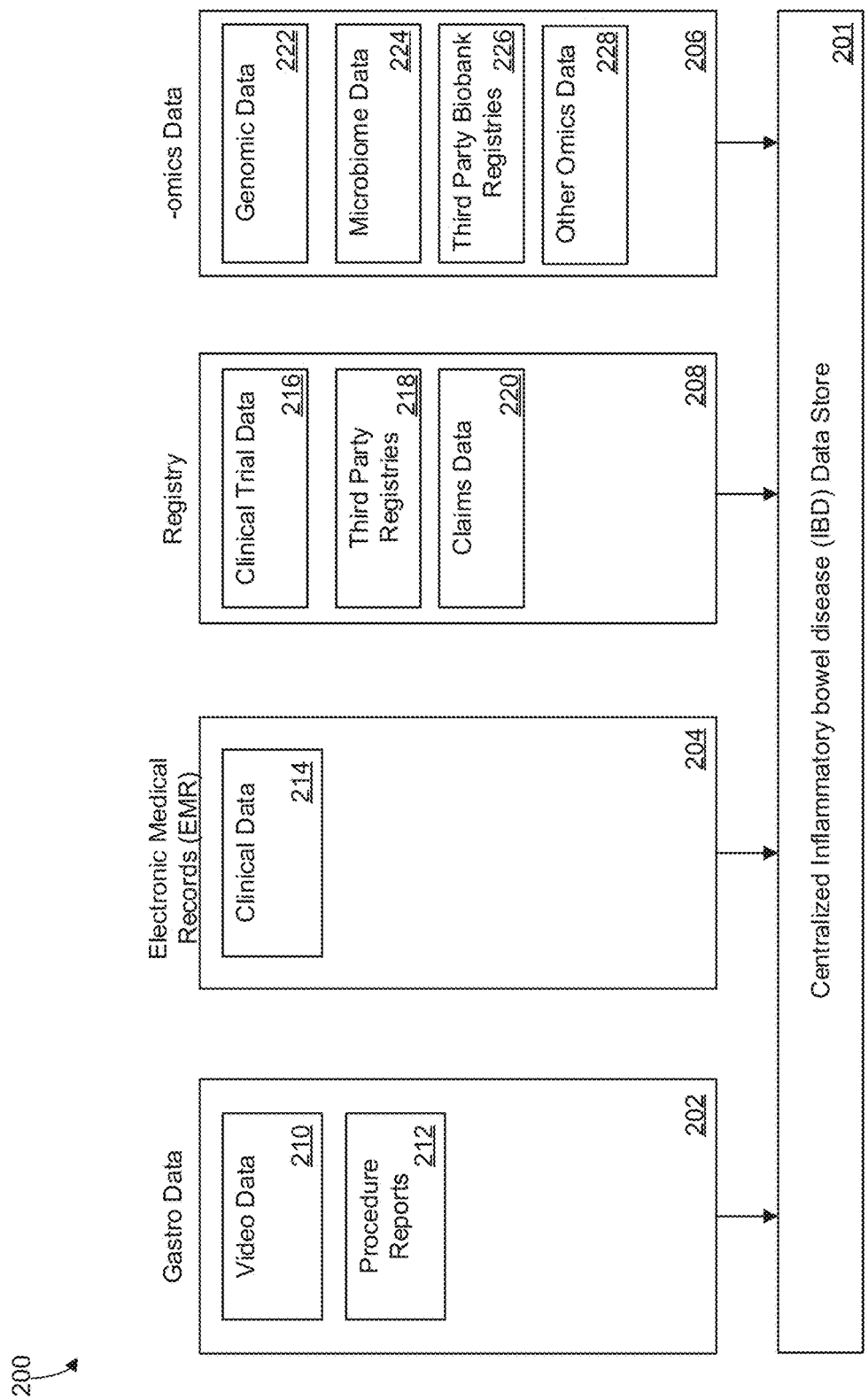
FIG. 2 shows example data sources for training and developing machine learning models for detection of IBD.

FIG. 2 shows example data sources 200 for training and developing machine learning models for detection of IBD activity. Data sources 200 correspond to data sources 103 of FIG. 1. The data processing system 100 of FIG. 1 can be configured to communicate with a centralized IBD data store 201. The centralized data store 201 is configured to communicate with each of the data sources including the gastro data 202, the EMR data 204 (e.g., similar to EMR data 104), the registry data 208 (e.g., similar to registry data 108), and the -omics data 206 (e.g., similar to -omics data 106 of FIG. 1). Generally, the centralized data store 201 can store data from multiple individual data sources 202, 204, 206, and 208 in a common structured system. For example, the data sources 202, 204, 206, and 208 can be 3rd party data sources or segmented data stores confined to particular data formats, particular data structures, and/or particular data accessible by particular systems. The centralized data store 201 retrieves data from the sources 202, 204, 206, and 208 can combine the data in to facilitate processing by the machine learning module 113, scoring module 115, and so forth for the data processing system 100.

The gastro data 202 generally includes data related to endoscopic procedures. For example, the gastro data 202 can include video data 210 (e.g., similar to the video data 102 previously described). The gastro data 202 can also include other data associated with the endoscopic procedure used to acquire the video data 210. For example, the gastro data 202 can include procedure reports 212 that include data about the patient when the procedure was performed, how the procedure was performed and what the video data represents (e.g., a particular region of the intestines or other portion of the body). The procedure reports 212 can include any data provided by the patient or the medical service provider that is related to the procedure.

The EMR data 204 include medical records for particular patients (similar to EMR data 104 previously described). The EMR data 204 can include data that conform to standard forms. The EMR data 204 can include clinical data for a patient that is provided by a medical service provider in response to a patient visit or telehealth interaction. Generally, the EMR data 204 are on a per-patient basis. This provides a rich history for a particular patient, and the patient's EMR data 204 can be imported to the centralized IBD data store 201 when the patient data is being processed by the data processing system 100.

The gastro data 202 includes features that are used for classifiers for the machine learning models subsequently described. The values of the feature data affect how the scoring is performed by the machine learning model. For example, an endoscopy classifier receives feature data describing the patient as received from endoscopy procedures of the patient. These features can be represented in the video data 102. The values of the features affect how the machine learning model classifies the score of the patient. The gastro data 202 features can include values that represent, for an endoscopy classifier, one or more of the following. The gastro data 202 features can include values that represent a location of the endoscopy, such as a lower GI endoscopy. The gastro data 202 features can include values that represent a presence of ulcers and/or a number of ulcers. The gastro data 202 features can include values that represent a relative vascularity, such as a percentage decrease of vascularity. The gastro data 202 features can include values that represent presence of erosions, and a number of the erosions. The gastro data 202 features can include values that represent presence or absence of bleeding in the GI tract, and a number of times bleeding was observed (e.g., a number of frames including evidence of bleeding). The gastro data 202 features can include values that represent erythema in GI tract). The gastro data 202 features can include values that represent a friability (e.g., in GI tract). The gastro data 202 features can include values that represent a size of ulcers or erosions. The gastro data 202 features can include values that represent a presence of stenosis (e.g., narrowings) of the GI tract. The gastro data 202 features can include values that are associated with an upper GI endoscopy (e.g., that specified as located in the upper GI endoscope data). The gastro data 202 features can include values that represent a total ulcerated surface (e.g., presence or absence of this surface, and a percentage of the tract including such a surface). The gastro data 202 features can include values that represent a surface affected by disease (e.g., as a percentage of the total surface). The gastro data 202 features can include values that represent a disease location in GI tract. The gastro data 202 features can include values that represent a number of lesions observed (e.g., at the case level). The gastro data 202 features can include values that represent a presence of cobblestoning in the tract. The gastro data 202 features can include values that represent a presence of deep ulcers. The gastro data 202 features can include values that represent a type of Crohn's disease observed (e.g., non-stricturing, non-penetrating, stricturing, penetrating, stricturing and penetrating, or perianal). The gastro data 202 features can include values that represent a presence of dysplasia in the patient. The gastro data 202 features can include values that represent whether activity at a biopsy site is proximal or distal. In some implementations, gastro data 202 can be a part of EMR data 204, subsequently described.

The EMR data 204 includes data representing features that are used for classifiers for the machine learning models subsequently described. For example, a concomitant medications classifier contributes a score based on whether these medications are being used by the patient. The data can include whether the patient is using diphenoxylate or opiates as anti-diarrheal medication. The values of the feature data affect how the scoring is performed by the machine learning model. In another example, a demographic classifier receives feature data including demographics data about the patient, which can affect how scoring is performed. For example, the demographics features can include age, sex, reproductive history, smoking status, and race or ethnicity. In another example, a physical examination classifier receives feature data including patient data obtained from physically examining the patient by a physician. For example, the features for this classifier can include data from a patient medical history which may indicate ileocolonic resection. The feature data can include data indicative of one or more of the presence or absence of an anal fissure, a fistula or abscess, and the presence or absence of one or more complications such as uveitis, pyoderma gangrenosum, erythema nodosum, and/or arthralgia. The feature data can include data from physicians' global assessment of the patient (e.g., indicating the presence or absence of a condition). The EMR data 204 features can include values from pathology laboratory results, such as representing serological profiling results for a time period. The feature data include data values representing a history of medications prescribed to the patient, including current medications and biologics. The EMR data 204 features can include values that represent whether the patient has used biologics. The EMR data 204 features can include values that represent disease activity (e.g., whether a disease is active or inactive). The EMR data 204 features can include values that represent an IBD type, such as whether the type includes UC or CD. The EMR data 204 features can include values that represent a disease duration (e.g., in years). The EMR data 204 features can include values that represent a history of surgery for the patient (e.g., whether it has occurred, what surgery has occurred, and when surgery has occurred). The EMR data 204 features can include values that represent whether steroid-free remission has occurred. The EMR data 204 features can include values that represent fistula drainage (e.g., an extent or occurrence). The EMR data 204 features can include values that represent whether the patient has experienced pain or activity restriction (e.g., frequency and severity values associated with either or both). The EMR data 204 features can include values that represent a degree of induration for the patient. The EMR data 204 features can include values that represent a presence or size of an abdominal mass in the patient. The EMR data 204 features can include values that represent whether sexual activity has been restricted. The EMR data 204 features can include values that represent a history of flaring (e.g., during a study associated with the patient). The EMR data 204 features can include values that represent a hospitalization history for the patient (e.g., time, duration, frequency, etc.). The EMR data 204 features can include values that represent a history of thrombosis for the patient (e.g., frequency, location, and/or severity).

In another example, the EMR data 204 features can be associated with an environmental classifier. The features can include results from the short IBD questionnaire (e.g., an SIBDQ). The features can include values representing a patient diet, such as whether dairy has been consumed. The features can include values representing environmental exposures of the patient, including whether over the counter (OTC) drugs have been consumed by the patient, patient infections (e.g., types, locations, frequencies, etc.), and whether the patient has traveled or undergone major life events that may contribute stress to the patient's life. The features can include values representing relevant family history of disease. The features can include values representing fecal incontinence in the patient in the past. In these examples, values for these features can affect the weightings of a neural network (or other machine learning model) used for generating scores, as subsequently described.

The registry 208 includes patient data across patient populations. The registries can include anonymized health data that relates health trends to particular symptoms, scores, patient phenotypes, and so forth. The registry data 208 can include data representing results for how different treatments for different stages of a disease (such as IBD) affected patients.

The registry data 208 includes clinical trial data 216. The clinical trial data include results and other data from studies, experiments, and clinical trials that test treatment regimens. The treatment regimens can include drug therapy, physical therapy, surgery, or other possible treatments.

The registry data 208 include third party registries 218. The registries 218 can be existing or established databases accessible by subscription or for free. These registries provide large amounts of data for a treatment space such as IBD that can help inform the machine learning module 113, and/or scoring module 115 as to how to score symptoms for IBD in a patient with particular symptoms or associated with a particular patient history.

The registry data 208 includes claims data 220. The claims data 220 includes billing codes or other standardized data that physicians, pharmacies, hospitals, and other medical service providers submit to payers (e.g., insurance companies, Medicare). Claims data 220 generally includes a standard format across a wide variety of systems. The codes associated with services performed are a standard set of pre-established codes that describe specific diagnoses, procedures, and drugs. Additionally, nearly every encounter that a patient has with the medical system leads to the generation of a claim, creating an abundant and standardized source of patient information. The claims data 208 can be used to determine how patients are generally interacting with healthcare, both at an individual level and across patient populations.

The -omics data 206 includes genetic or molecular profiles of patient populations. The omics data 206 can provide a context as to how a given patient responds to a given treatment. Patients may be grouped by common expressions shown in omics data 206, and the machine learning module 113 can generate scores based on correlations found in the data. Generally, the omics data 206 include genomics, which include a patient genome or genomic data 222. The omics data 206 include proteomics data representing sets of proteins produced by an organism. The omics data 206 include transcriptomics data such as sets of RNA molecules, including mRNA, rRNA, tRNA, and other non-coding RNAs relevant to treatment outcomes. The omics data 206 include pharmacogenomics data representing an effect of variations within the human genome on response to drugs. The omics data represent phenotypic traits, such as comprehensive description of disease symptoms in a patient. Additionally, the omics data 206 can include microbiome data 224 and third party biobank registries 226 including any of the foregoing data. Other omics data 228 can also be included.

In some implementations, the omics data 206 includes data representing features that are used for classifiers for the machine learning models subsequently described. For example, a genomic classifier can be applied to the omics data 206. The -omics data 206 can include feature data having values representing genome sequencing from blood for analysis by the molecular genomics classifier. Other feature data for the molecular genomics classifier can include bisulfite sequencing (RRBS) data from blood of the patient. The -omics data 206 can include feature data having values representing ChIP-sequencing for the patient and/or other patients. The -omics data 206 can include feature data having values representing HLA-DR genotyping for the patient and/or other patients. In some implementations, the DNA can be extracted from either blood or saliva of a patient. Conversely RNA can be extracted from either is the basis of transcriptomics. mRNA is used in proteomics. CHIP is a particular test that links protein and DNA. The -omics data 206 can include feature data having values representing genome sequencing from saliva of the patient.

In another example, a molecular microbiome classifier can be applied to the omics data 206. The -omics data 206 can include feature data having values representing a 16s microbiome sequence from stool of the patient and/or a 16s microbiome sequence from a biopsy of the patient. In some implementations, the -omics data 206 can include feature data having values representing metagenomics, metatranscriptomic information, metabolite profiling results for the patient, and/or virome data associated with the patient.

In another example, a molecular classifier can be applied to the omics data 206. The -omics data 206 can include feature data having values representing epithelial cell profiling from biopsy of the patient and/or single cell assay from a biopsy of the patient.

In another example, a transcriptomics classifier can be applied to the omics data 206. The -omics data 206 can include feature data having values representing a transcriptome sequence from a biopsy of the patient and/or a single-cell RNA sequence from a biopsy of the patient. In some implementations, the data can include proteomics data (e.g., proteomic sequencing) as feature data. In these examples, values for these features can affect the weightings of a neural network (or other machine learning model) used for generating scores, as subsequently described.

In another example, a laboratory results classifier can be applied to laboratory results from the patient. The results can be included in the -omics data, registry data 208, and/or EMR data 204. The laboratory results data can include feature data having values representing an activity of a blood sample of the patient. The laboratory results data can include feature data having values representing fecal calprotectin or lactoferrin of the patient. The laboratory results data can include feature data having values representing Haematocrit levels for the patient, either at a point in time or over a period of time. The laboratory results data can include feature data having values representing serum CRP/C-reactive protein levels in the patient. The laboratory results data can include feature data having values representing Pharmacokinetics (PK) data associated with a patient (such as in response to a drug therapy). The laboratory results data can include feature data having values representing histology results for the patient. The laboratory results data can include feature data having values representing a full blood analysis of the patient, including values for white blood cell counts (WBC), hemoglobin (HgB), platelets, albumin, creatinine, and/or ESR levels. The laboratory results data can include feature data having values representing a urea analysis of the patient. The laboratory results data can include feature data having values representing liver function tests of the patient. The laboratory results data can include feature data having values representing ferritin, B12, Folate and VitD levels in the patient. The laboratory results data can include feature data having values representing SCFA levels in stool of the patient. The laboratory results data can include feature data having values representing basal metabolite panel in the patient. The laboratory results data can include feature data having values representing one or more tests, such as a fecal lactoferrin test and/or a fecal occult blood test (FOBT). The laboratory results data can include feature data having values representing blood tests to identify perinuclear anti-neutrophil cytoplasmic antibodies (pANCA), anti-*Saccharomyces cerevisiae* antibodies (ASCA), anti_CBirl_antibodies, and/or anti_OmpC_antibodies. In these examples, values for these features can affect the weightings of a neural network (or other machine learning model) used for generating scores, as subsequently described.

In another example, a symptoms classifier can be applied to symptoms data from the patient. The results can be included in the -omics data, registry data 208, and/or EMR data 204. The symptoms data can include feature data having values representing a number of liquid stool per week for a patient, a bowel frequency for the patient, data representing rectal bleeding in the patient (e.g., frequency and severity), a general well-being of the patient (e.g., from survey data), abdominal pain during a week as reported by the patient, an urgency of defecation reported by the patient, and so forth.

Generally, the gastro data 202, the EMR data 204, the registry data 208, and the omics data 206 are stored as structured data in the centralized IBD data store 201. Features can be extracted from any of the data stored in the data store 201 for use during classification by the machine learning module 113, scoring by the scoring module 115.

Figure 3:
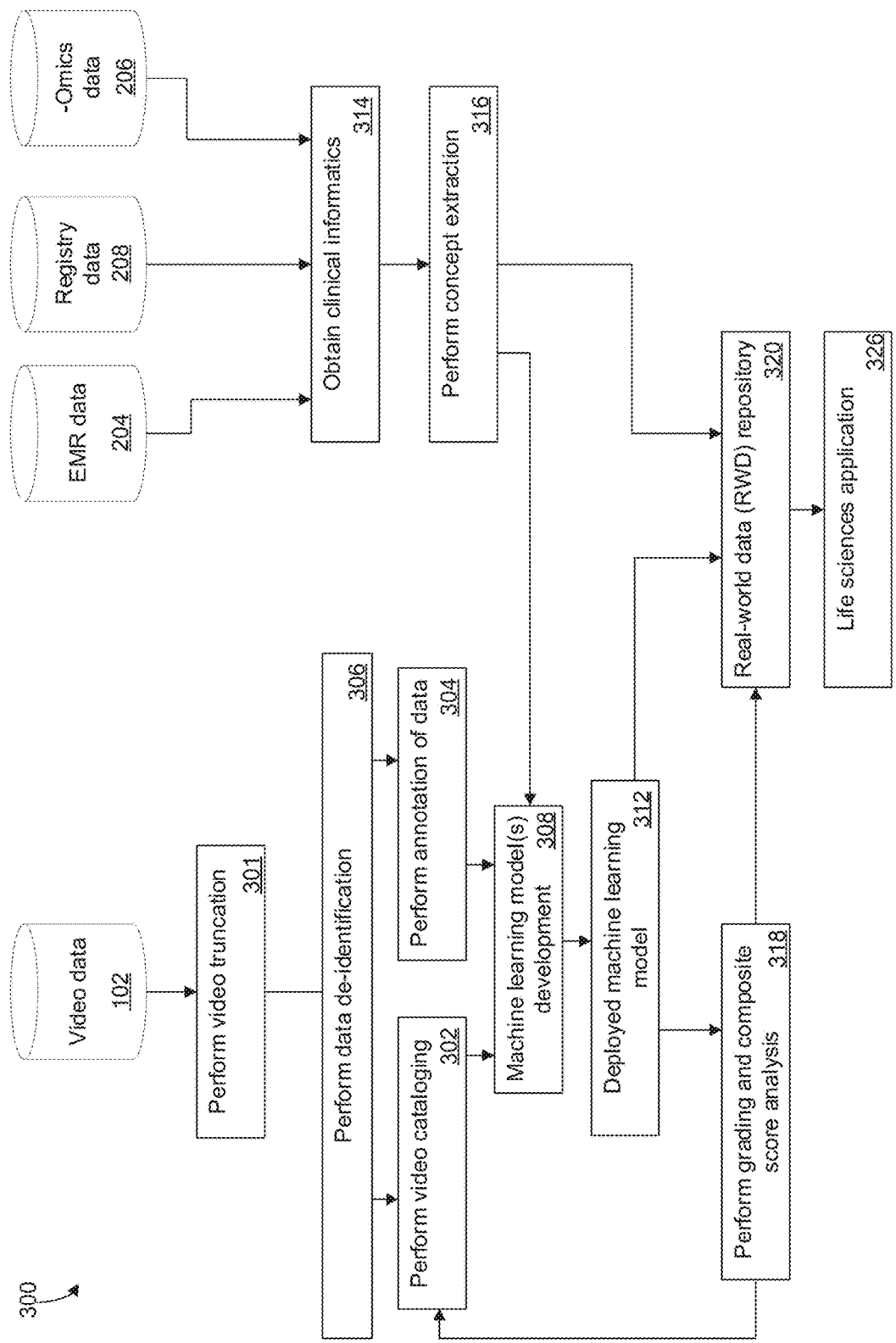
FIG. 3 shows examples of data processes for training and developing machine learning models for prediction of each of IBD severity and treatment outcomes.

FIG. 3 shows examples of data processes 300 for training and developing machine learning models for scoring of each of IBD severity (e.g., by machine learning module 113 of FIG. 1). The process 300 includes receiving video data 102, EMR data 204, registry data 208, and omics data 206. While these data 102, 204, 206, and 208 are specifically discussed, other data (as previously described) can be incorporated into the machine learning model.

The machine learning module 113 is configured to perform (301) video truncation to extract video data for processing. Truncation can include removing portions of the video data that are not relevant to the scoring process because the portions do not include relevant data, include redundant data, or include data that is noisy or otherwise unusable (e.g., image frames that are out of focus, not illuminated, and so forth).

The machine learning module 113 is configured to de-identify (306) the video data. This can include data masking, anonymization, data scrambling, removal of portions of the data, and so forth. In some implementations, the de-identification of the video data can be performed by another module or system besides the machine learning model 113. For example, the de-identification of the data can be performed by an interfacing module before any data are processed by the machine learning model 113. In another example, the de-identification of the data can be performed prior to storage of the data 102, so that data accessed the data processing system are already anonymized.

The machine learning module 113 is configured to perform (302) video cataloging. This includes structuring the video data 102 based on metadata associated with the video data. The metadata may be generated when the video data are generated, or can be associated with the video data during cataloging. The metadata may include identifications of an operation associated with the video data 102, a timestamp, and so forth.

The machine learning module 113 is configured to perform (304) annotation of the video data 102. The annotation is based on image processing of the video. Annotations can be associated with each video frame, or with portions of the video clip. This can provide both frame-level data, which includes annotations associated with individual frames of the video data 102. Frame level annotations can include data relevant to a particular frame. For example, the frame level annotations may include data represented whether bleeding is observed, a number of polyps, in the image, and/or a location in the tract associated with the particular image frame. The annotations are also case level annotations, which include annotations describing entire videos including multiple image frames. The case level annotations include information about the video overall, such as aggregates of annotations stored with individual frames. This can include annotations indicating that, for example, bleeding was observed a particular number of times in the video, or not at all. In another example, a total number of polyps that were observed can be included in the case level annotations. In another example, a percentage of frames including polyps, bleeding, neither, or both can be included in the annotations. Other such annotations can be included at the case level. In some implementations, the training can be assisted by manual review.

After de-identification, the machine learning module 113 is further developed (308) based on receiving data from the additional sources 103, such as EMR data 104, registry data 208, and omics data 206. The machine learning module 113 obtains (314) clinical informatics for each of these data sources. This can include structuring the data (e.g., in the centralized database 201 of FIG. 2). In some implementations, the informatics are obtained by identifying an existing structure for the data 204, 206, and 208. In some implementations, the process 300 includes feature extraction (316) from these data by the machine learning module 113. These data 104, 106, 108 are also de-identified (306) for use in the machine learning model. These data can also be stored (320) as real world data (RWD) in a database. This database can be used for one or more downstream applications (326).

The machine learning module 113 is developed (308) using one or more of the data 102, 204, 206, and 208, as subsequently described. The machine learning module 113 can include, for example, a trained classifier, convolutional neural network, recurrent neural network, support vector machine, or other such machine learning model. The machine learning module 113 is configured to train the model using one or more of the data 102, 204, 206, and 208.

The process 300 includes deploying (312), by the machine learning module 113, the machine learning model that is trained. The machine learning module 113 is configured to perform endo-grading (318) of the video data 102 based on the trained machine learning model. This process includes a composite score analysis. Generally, a neural network is used for which various streams (e.g., segmentation, regression, and clip-level results) are combined into an input.

When more than one machine learning model is used to analyze the video data 102, the scores generated by each of the models are combined into a composite score. The combination process can be a voting system, a weighted average, or a similar process. The composite score can be determined from multiple frame scores such that a composite score is developed for each frame. In some implementations, a composite score is developed for each video based on a combination composite frame scores or based on a combination of video scores from each of the models.

Figure 4:
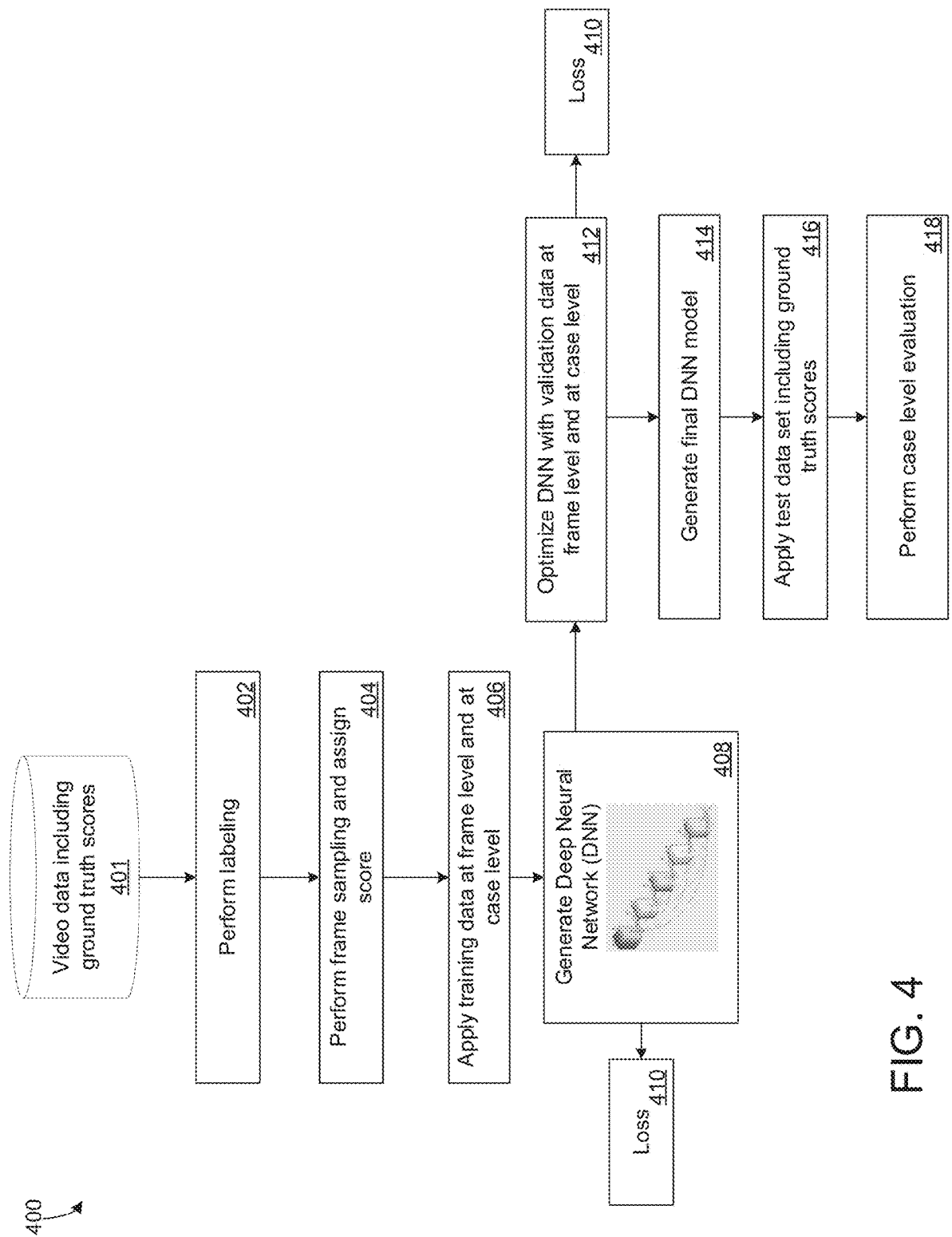
FIG. 4 show an example flow diagram for performing automated regression analysis for detection of IBD.

FIG. 4 show an example flow diagram of a process 400 for performing automated regression analysis for detection of IBD (e.g., by the machine learning module 113 of FIG. 1). The process 400 includes obtaining video data including ground truth scores 401. The ground truth scores represent the expected result of a machine learning model (e.g., a correct classification, given a set of inputs). Process 400 is configured to tune the parameters of a machine learning model for generating scores for IBD in patients such that the ground truth scores are accurately calibrated for the model. The ground truth scores associated with the image data 401 can be manually added or determined using other available data (e.g., from centralized data store 201 of FIG. 2). The process 400 includes performing (402), by an image processing module (e.g., module 114 of FIG. 1), labeling of the video data, wherein the labels include labels associated with individual frames of the videos, entire videos, or combinations thereof. The process 400 includes performing (404) frame sampling for the video data that is labeled. A score is assigned to each frame of the video or to each frame of a subset of the frames.

The process 400 includes applying training data 406 to train a machine learning model 408 (such as a model of module 113 of FIG. 1). The training data can include data with either or both frame level annotations and case level annotations. The model 408 of the machine learning module 113 is trained using the training data 406 generated from the frame sampled data. Weight values and activation values are tuned for the machine learning model 408, which can be a deep neural network (DNN) or other similar model. Loss values 410 are generated. A loss value 410 represents a penalty for a bad score and can be used to optimize (412) the model 408 until loss values approach zero.

The model 408 is optimized using validation data. The validation data further refine the model 408. The validation data generally include "new" data that are annotated with either or both frame level annotations and case level annotations. The validation data are used to ensure that the model 408 is outputting expected results based on the annotated data being processed by the model 508. The model 408 is refined until a final model 414 results, where the final model is a validated model.

The validated model 414 is executed (416) on a test data set to evaluate outcomes of the model 414. The test data are pristine, non-annotated data that have not yet been processed by the model 414. The test data are processed using the established ground truth scores of the model 414. Generally, the test data are used to perform (418) case level evaluation of the model 414. The validation dataset can include known classifications or other data that indicate a classification or otherwise train the machine learning model. A test dataset can also be applied which includes pristine, unannotated data to test the model 414. The test dataset can be manually evaluated to determine whether the model 414 is operating as intended with unseen data.

The data previously described is obtained and used in the process 400 to generate the classifiers that were previously described. These classifiers can be used individually and/or in combination to generate score data for the patient. For example, the gastro data 202, the EMR data 204 registry data 208 and/or the -omics data 206 previously described are used to train, validate, and test one or more classifiers. The classifiers can include, as previously described, a concomitant medications classifier, a demographic classifier, an endoscopy classifier, an environmental classifier, a genomics classifier, a laboratory results classifier, a microbiome classifier, a patient medical history classifier, a physical examination classifier, a proteomics classifier, a symptoms classifier, and/or a transcriptomics classifier, or any combination thereof.

In some implementations, the above described classifiers can be combined to generate the score for IBD for a patient. In some implementations, a statistical combination of the classifier outputs can be used. For example, these can include combining the outputs of the classifiers based on a function of each output of the classifiers. For example, the function can include a weighted average, a voting system, a ratio, or some other combination of the classifier output values. In some implementations, the classifier outputs can be combined into an input vector for another machine learning model that receives the classifier outputs as input values. This can be called a second order machine learning model. The second order machine learning model can include any of the machine learning models previously or subsequently described. Additionally, the second order machine learning model can be trained with example classifier outputs in a similar manner as previously described for the machine learning models of the classifiers.

In some implementations, the model 414 includes a convolutional neural network (CNN). A convolutional neural network (CNN) can be configured based on a presumption that inputs to the neural network correspond to image pixel data for an image or other data that includes features at multiple spatial locations. For example, sets of inputs can form a multi-dimensional data structure, such as a tensor, that represent color features of an example digital image (e.g., an image of the surroundings of a vehicle). In some implementations, inputs to the neural network correspond to a variety of other types of data, such as data obtained from different devices and sensors of a vehicle, point cloud data, audio data that includes certain features or raw audio at each of multiple time steps, or various types of one-dimensional or multiple dimensional data. A convolutional layer of the convolutional neural network can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which a system performs the computations can be based on specific properties for each layer of an example multi-layer neural network or deep neural network that supports deep neural net workloads. A deep neural network can include one or more convolutional towers (or layers) along with other computational layers. In particular, for example computer vision applications, these convolutional towers often account for a large proportion of the inference calculations that are performed. Convolutional layers of a CNN can have sets of artificial neurons that are arranged in three dimensions, a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R-G-B. A convolutional layer of a neural network of the model 414 computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer. That is, for each kernel or set of kernels, the model 414 can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The model 414 is configured to compute, when executed by the machine learning module 113, a dot product from the overlapped elements. For example, the model 414, by the machine learning module 113, is configured to convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The model 414, by the machine learning module 113 convolves each kernel over each input of an input volume. The model 414, by the machine learning module 113, performs this convolution operation by, for example, moving (or sliding) each kernel over each input in the region.

The model 414, by the machine learning module 113, moves each kernel over inputs of the region based on a stride value for a given convolutional layer. For example, when the stride is set to 1, then the model 414 moves the kernels over the region one pixel (or input) at a time. Likewise, when the stride is 2, then the model 414 moves the kernels over the region two pixels at a time. Thus, kernels may be shifted based on a stride value for a layer and the model 414 can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the model 414 produces a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the neural network.

An example convolutional layer can have one or more control parameters for the layer that represent properties of the layer. For example, the control parameters can include a number of kernels, K, the spatial extent of the kernels, F, the stride (or skip), S, and the amount of zero padding, P. Numerical values for these parameters, the inputs to the layer, and the parameter values of the kernel for the layer shape the computations that occur at the layer and the size of the output volume for the layer. In one implementation, the spatial size of the output volume is computed as a function of the input volume size, W, using the formula (W?F+2P)/S+1. For example, an input tensor can represent a pixel input volume of size [227×227×3]. A convolutional layer of a neural network can have a spatial extent value of F=11, a stride value of S=4, and no zero-padding (P=0). Using the above formula and a layer kernel quantity of K=96, the model 414 performs computations for the layer that results in a convolutional layer output volume of size [55×55×96], where 55 is obtained from [(227−11+0)/4+1=55].

The computations (e.g., dot product computations) for a convolutional layer, or other layers, of a neural network involve performing mathematical operations, e.g., multiplication and addition, using a computation unit of a hardware circuit of the model 414. The design of a hardware circuit can cause a system to be limited in its ability to fully utilize computing cells of the circuit when performing computations for layers of a neural network.

Based on the aforementioned techniques, the model 414 is configured to identify locations of potential malignancies in images. In some implementations, potential malignancies include polyps. In some implementations, given a set of images, the model 414 is capable of correctly detecting at least 87% of all polyps shown (e.g., at least one image of at least 87% of the polyps presented in the set of images will be correctly detected and identified). In some implementations, when given a set of images, and the model 414 is capable of making a determination that an image does not contain a polyp, and that determination is correct at least 98.7% of the time (e.g., it is likely to be correct 98.7% of the times the machine learning 113 system makes a "does not contain polyp" classification).

In some implementations, the model 414 includes other types of digital neural networks, such as a recurrent neural network (RNN), a radial basis function network, a deconvolution network, a variational auto-encoder (VAE), generative adversarial network (GAN) and so forth.

Figure 5:
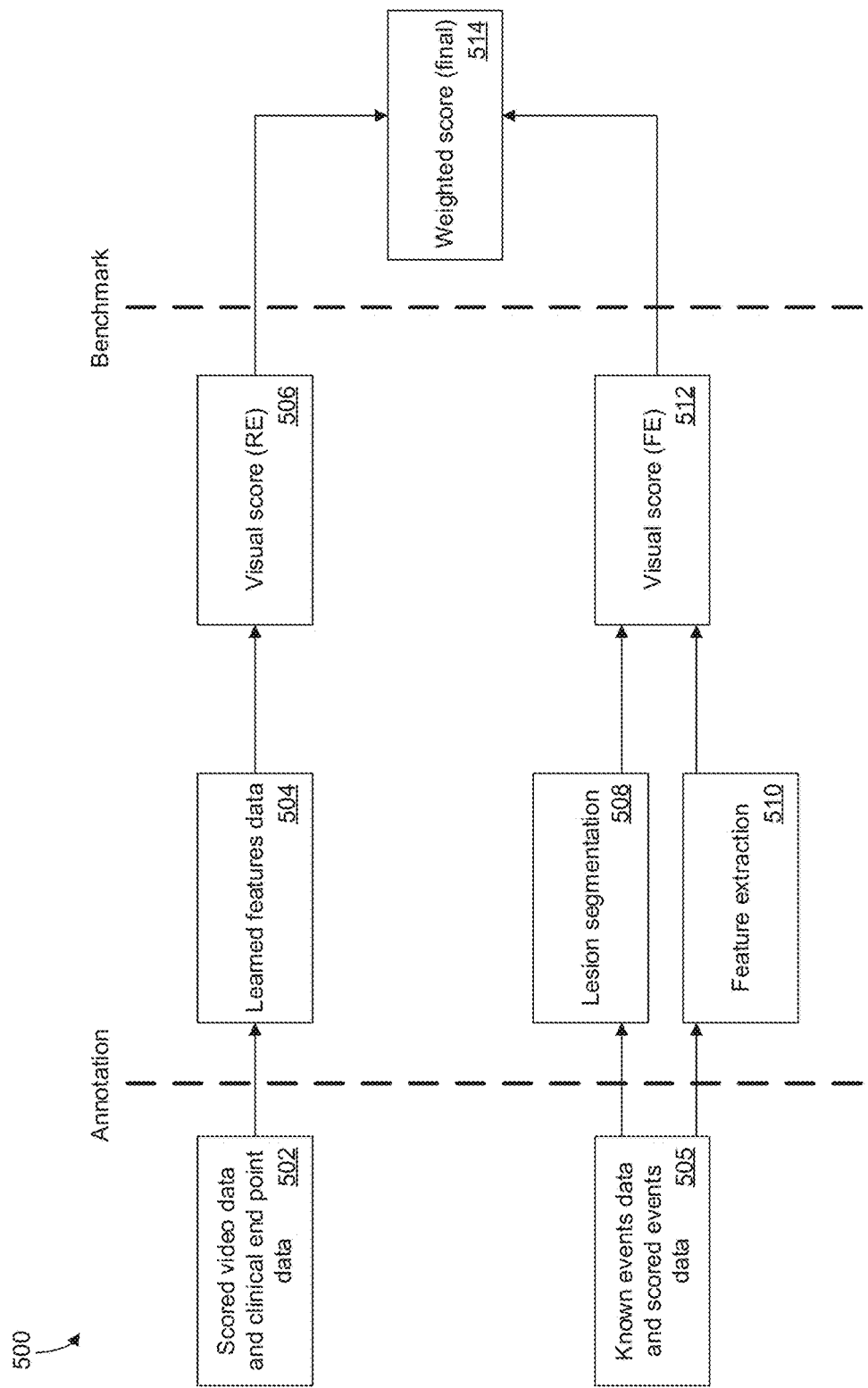
FIG. 5 shows an example flow diagram for a multi-pronged ML process for tracking IBD severity and for predicting future IBD severity.

FIG. 5 shows an example flow diagram for a multi-pronged ML process 500 for tracking IBD severity and for classifying IBD severity. The process 500 includes annotation portions and benchmarking portions. In a first prong, the process 500 includes obtaining (502) scored video data and clinical endpoint data. The process 500 includes generating (504) learned features data. The process 500 includes generating (506) a visual score (RE) (e.g., as described in relation to FIG. 1).

In a second prong, the process 500 includes obtaining (505) known events data and scored events data. The process 500 includes performing lesion segmentation (508) and feature extraction (510) from the events data and scored events data. The process 500 includes generating (512) a visual score (FE) (e.g., as described above in relation to FIG. 1). The process 500 includes generating (514) a combined, weighted score from the FE score and the RE score.

Figure 6:
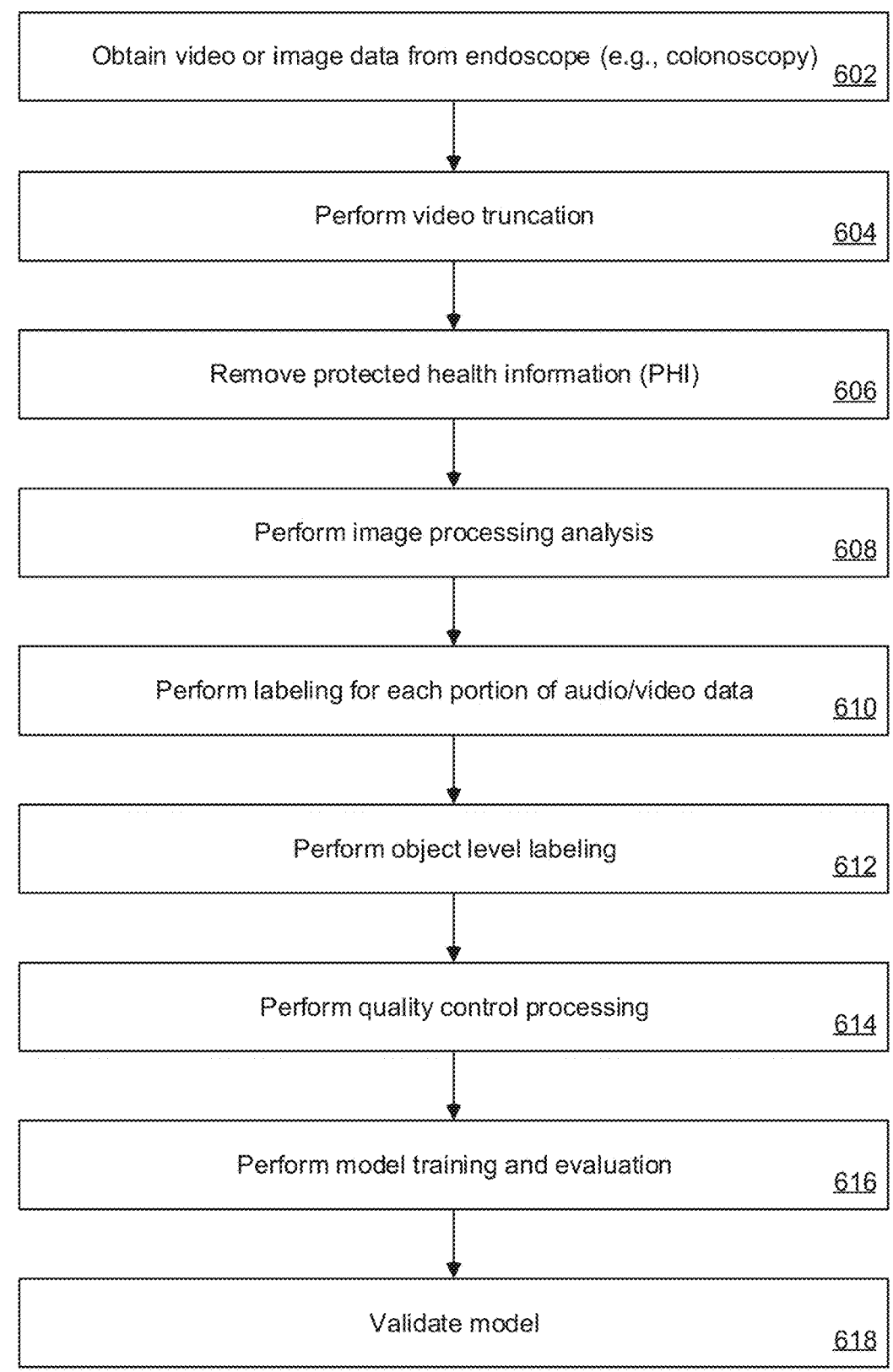
FIG. 6 shows a flow diagram for scoring IBD.

FIG. 6 shows a flow diagram showing a process 600 for scoring IBD. The process 600 includes obtaining (602) video or image data from endoscope (e.g., colonoscopy). The process 600 includes performing truncation (604) of the video or image data. The process 600 includes performing (606) an image processing analysis. The process 600 includes removing (608) personally identifying information, such as protected health information (PHI). The process 600 includes performing labeling (610) for each portion of audio/video data. The process 600 includes performing (612) object level labeling. The process 600 includes performing quality control processing (614). The process 600 includes performing model training and evaluation (616). The process 600 includes validating (618) the model. In some implementations, the process 600 includes receiving, from an imaging device, medical images that include endoscopy data. The process 600 includes applying a machine learning model to the medical images to determine one or more measurements of inflammation or other physical characteristic related to IBD. The machine learning model combines image classification with detection bounding boxes and segmentation pixel-wise masks. The process 600 includes obtaining electronic health data of patient. The process 600 includes combining the electronic health data of patient onto the one or more measurements of inflammation including the bounding boxes and pixel-wise masks. The process 600 includes generating, based on the combining, a score indicative of a progression of IBD in the patent. The process 600 includes generating an output that indicates prediction severity of IBD in the patient.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A method for treatment of inflammatory bowel disease (IBD) in a patient and determining a score of disease activity, the method comprising:
    obtaining image data including endoscopic images of a gastrointestinal tract (GI) of a patient;
    determining one or more features to extract from the image data, the features each representing a physical parameter of the GI tract;
    extracting the one or more features from the image data to form feature data;
    selecting a machine learning model based on the one or more features included in the feature data;
    processing the feature data using the machine learning model, the machine learning model being trained with labeled image data representing instances of symptoms of IBD being in the GI tract, the labeled image data associating scores representing a severity of IBD the respective instances of the symptoms, wherein processing the feature data includes:
    generating one or more frame level annotations corresponding to one or more individual frames the image data; and
    accessing context data representing analysis for IBD severity for one or more previous frames to the one or more frames or representing analysis for IBD severity for one or more subsequent frames of the one or more frames;
    determining, based on the processing and based on the one or more frame level annotations and the context data, a score representing a severity of IBD in the patient indicated by the image data; and
    storing, in a data store, the score in association with the image data.

2. The method of claim 1, wherein determining the score comprises:
    determining one or more case level annotations for a video of the image data;
    generating a temporal annotation for a subsequent frame of at least one of the one or more individual frames, the temporal annotation based on content in the subsequent fame and state data describing the at least one of the one or more individual frames; and
    determining, based on the one or more frame level annotations, the temporal annotation, and the one or more case level annotations, the score associated with the video of the image data.

3. The method of claim 1, wherein the one or more features comprise values representing at least one of:
    a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal; and
    wherein the score represents a severity of IBD in the patient is based on the values of the one or more features.

4. The method of claim 1, further comprising:
    receiving electronic medical records (EMR) data for the patient, the EMR data including medical information about the patient, wherein the machine learning model is trained with labeled EMR data associating values of medical information of patients with respective severity of IBD in the patients;
    extracting one or more values from the EMR data to form EMR feature data;
    processing, by the machine learning model or by a second machine learning model in addition to the machine learning model, the EMR feature data; and
    generating an updated score representing the severity of IBD in the patient indicated by the EMR data.

5. The method of claim 4, wherein the one or more features of the EMR feature data comprise values representing at least one of:
    an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

6. The method of claim 1, further comprising:
    receiving registry data for the patient, the registry data including patient data across patient populations, wherein the machine learning model is trained with labeled registry data associating values of for patient populations with respective severity of IBD in particular patients of the patient populations;
    extracting one or more values from the registry data to form registry feature data;
    processing, by the machine learning model or by a second machine learning model in addition to the machine learning model, the registry feature data; and
    generating an updated score representing the severity of IBD in the patient indicated by the registry data.

7. The method of claim 6, wherein the one or more features of the registry feature data comprise values representing at least one of:
    results and other data from studies, experiments, and clinical trials that test treatment regimens that are associated with the patient including one or more of drug therapy, physical therapy, or surgery, specific diagnoses associated with the patient, procedures, and application of drugs associated with the patient.

8. The method of claim 1, further comprising:
receiving omics data for the patient, the omics data including genetic or molecular profiles of patient populations, wherein the machine learning model is trained with labeled omics data associating values of genetic or molecular profiles with respective severity of IBD in the patients of the patient populations;
extracting one or more values from the omics data to form omics feature data;
processing, by the machine learning model or by a second machine learning model in addition to the machine learning model, the omics feature data; and
generating an updated score representing the severity of IBD in the patient indicated by the omics data.

9. The method of claim 8, wherein the one or more features of the omics feature data comprise values representing at least one of:
transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfite sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

10. The method of claim 1, wherein the machine learning model comprises a convolutional neural network (CNN), and wherein the each of the instances of symptoms of IBD contributes to an activation value for inputting into a layer of the CNN.

11. The method of claim 1, wherein processing the feature data comprises performing a classification with detection bounding boxes and segmentation pixel-wise masks on the image data.

12. The method of claim 1, further comprising generating the machine learning model by:
receiving image data including ground truth scores;
labeling the image data;
performing frame sampling and score assignment to the frames;
applying training data to the machine learning model at a frame level and at a case level;
optimizing the machine learning model with validation data at the frame level and the case level;
applying test data that is not annotated; and
performing case level evaluation of the test data.

13. A system for treatment of inflammatory bowel disease (IBD) in a patient and determining a score of disease activity, the system comprising:
one or more processing devices; and
a memory storing instructions that, when executed by the one or more processing devices, cause the one or more processing devices to perform operations comprising:
obtaining image data including endoscopic images of a gastrointestinal tract (GI) of a patient;
determining one or more features to extract from the image data, the features each representing a physical parameter of the GI tract;
extracting the one or more features from the image data to form a feature data;
selecting a machine learning model based on the one or more features included in the feature data;
processing the feature data using the machine learning model, the machine learning model being trained with labeled image data representing instances of symptoms of IBD being in the GI tract, the labeled image data associating scores representing a severity of IBD the respective instances of the symptoms, wherein processing the feature data includes:
generating one or more frame level annotations corresponding to one or more individual frames the image data; and
accessing context data representing analysis for IBD severity for one or more previous frames to the one or more frames or representing analysis of analysis for IBD severity for one or more subsequent frames of the one or more frames;
determining, based on the processing and based on the one or more frame level annotations and the context data, a score representing a severity of IBD in the patient indicated by the image data; and
storing, in a data store, the score in association with the image data.

14. The system of claim 13, wherein determining the score comprises:
determining one or more case level annotations for a video of the image data;
generating a temporal annotation for a subsequent frame of at least one of the one or more individual frames, the temporal annotation based on content in the subsequent fame and state data describing the at least one of the one or more individual frames; and
determining, based on the one or more frame level annotations, the temporal annotation, and the one or more case level annotations, the score associated with the video of the image data.

15. The system of claim 13, wherein the one or more features comprise values representing at least one of:
a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal; and
wherein the score represents a severity of IBD in the patient is based on the values of the one or more features.

16. The system of claim 13, the operations further comprising:

receiving electronic medical records (EMR) data for the patient, the EMR data including medical information about the patient, wherein the machine learning model is trained with labeled EMR data associating values of medical information of patients with respective severity of IBD in the patients;

extracting one or more values from the EMR data to form EMR feature data;

processing, by the machine learning model or by a second machine learning model in addition to the machine learning model, the EMR feature data; and generating an updated score representing the severity of IBD in the patient indicated by the EMR data.

17. The system of claim 13, the operations further comprising:

receiving registry data for the patient, the registry data including patient data across patient populations, wherein the machine learning model is trained with labeled registry data associating values of for patient populations with respective severity of IBD in particular patients of the patient populations;

extracting one or more values from the registry data to form registry feature data;

processing, by the machine learning model or by a second machine learning model in addition to the machine learning model, the registry feature data; and generating an updated score representing the severity of IBD in the patient indicated by the registry data.

18. The system of claim 13, the operations further comprising:

receiving omics data for the patient, the omics data including genetic or molecular profiles of patient populations, wherein the machine learning model is trained with labeled omics data associating values of genetic or molecular profiles with respective severity of IBD in the patients of the patient populations;

extracting one or more values from the omics data to form omics feature data;

processing, by the machine learning model or by a second machine learning model in addition to the machine learning model, the omics feature data; and generating an updated score representing the severity of IBD in the patient indicated by the omics data.

19. The system of claim 13, the operations further comprising;

generating the machine learning model by:

receiving image data including ground truth scores;

labeling the image data;

performing frame sampling and score assignment to the frames;

applying training data to the machine learning model at a frame level and at a case level;

optimizing the machine learning model with validation data at the frame level and the case level;

applying test data that is not annotated; and performing case level evaluation of the test data.

20. One or more non-transitory computer readable media storing instructions for treatment of inflammatory bowel disease (IBD) in a patient and determining a score of disease activity, wherein the instructions, when executed by one or more processing devices, cause the one or more processing devices to perform operations comprising:

obtaining image data including endoscopic images of a gastrointestinal tract (GI) of a patient;

determining one or more features to extract from the image data, the features each representing a physical parameter of the GI tract;

extracting the one or more features from the image data to form feature data;

selecting a machine learning model based on the one or more features included in the feature data;

processing the feature vector using the machine learning model, the machine learning model being trained with labeled image data representing instances of symptoms of IBD being in the GI tract, the labeled image data associating scores representing a severity of IBD the respective instances of the symptoms, wherein processing the feature vector includes:

generating one or more frame level annotations corresponding to one or more individual frames the image data; and accessing context data representing analysis for IBD severity for one or more previous frames to the one or more frames or representing analysis of analysis for IBD severity for one or more subsequent frames of the one or more frames;

determining, based on the processing and based on the one or more frame level annotations and the context data, a score representing a severity of IBD in the patient indicated by the image data; and storing, in a data store, the score in association with the image data.

* * * * *